(12) United States Patent
Castillo

(10) Patent No.: US 10,556,095 B2
(45) Date of Patent: *Feb. 11, 2020

(54) GOOGLE BREATHING SYSTEM

(71) Applicant: James D. Castillo, Los Alamos, CA (US)

(72) Inventor: James D. Castillo, Los Alamos, CA (US)

(*) Notice: Subject to any disclaimer, the term of this patent is extended or adjusted under 35 U.S.C. 154(b) by 338 days.

This patent is subject to a terminal disclaimer.

(21) Appl. No.: 14/799,192

(22) Filed: Jul. 14, 2015

(65) Prior Publication Data

US 2015/0314113 A1 Nov. 5, 2015

Related U.S. Application Data

(63) Continuation-in-part of application No. 14/622,448, filed on Feb. 13, 2015, now Pat. No. 9,283,106, which is a continuation-in-part of application No. 14/502,348, filed on Sep. 30, 2014, now Pat. No. 9,675,493.

(Continued)

(51) Int. Cl.
*A61M 29/00* (2006.01)

(52) U.S. Cl.
CPC .................. A61M 29/00 (2013.01)

(58) Field of Classification Search
CPC .. A61F 5/08; A61F 5/56; A61M 29/00; A61B 17/24
See application file for complete search history.

(56) References Cited

U.S. PATENT DOCUMENTS 3,835,848 A  9/1974 Berner
4,835,506 A  5/1989 Leupold
(Continued)

FOREIGN PATENT DOCUMENTS

CN  1389185  1/2003
JP  H10192412  7/1998
(Continued)

OTHER PUBLICATIONS

"3M Micropore Surgical Tapes: Commonly Asked Questions", Apr. 29, 2003, p. 1.*
(Continued)

*Primary Examiner* — Ashley L Fishback
(74) *Attorney, Agent, or Firm* — Stetina Brunda Garred and Brucker

(57) ABSTRACT

A breathing enhancement system for use with eyewear having a compressible liner. The breathing enhancement system includes a pair of clips configured to be selectively attachable to the eyewear and adapted to compress the compressible liner when attached to the eyewear to define a compressed portion of the compressible liner. A clip liner is adapted to engage with and extend between the pair of clips, with the clip liner being configured to reside within the compressed portion of the compressible liner. A pair of nasal appliques are configured to be selectively placeable on respective lateral portions the nose of a user, with each nasal applique being adapted to be magnetically urged toward a respective one of the pair of clips in response to placement of the eyewear adjacent the nose of the user to cause the nasal passage of the user to open.

20 Claims, 11 Drawing Sheets

Related U.S. Application Data

(60) Provisional application No. 61/937,018, filed on Feb. 7, 2014, provisional application No. 61/918,826, filed on Dec. 20, 2013.

(56) References Cited

U.S. PATENT DOCUMENTS

| | | | |
|---|---|---|---|
| 4,886,349 | A | 12/1989 | Willis |
| 5,533,503 | A | 7/1996 | Doubek et al. |
| 5,566,503 | A | 7/1996 | Doubek et al. |
| 5,546,929 | A * | 8/1996 | Muchin .................. A61F 5/08 128/200.24 |
| 5,719,655 | A | 2/1998 | Peschel et al. |
| 5,890,486 | A * | 4/1999 | Mitra .................. A61F 5/08 128/200.24 |
| 5,913,873 | A | 6/1999 | Blach et al. |
| 5,957,126 | A | 9/1999 | Neeser |
| 6,006,746 | A | 12/1999 | Karell |
| 6,033,422 | A | 3/2000 | Blach et al. |
| 6,352,548 | B1 | 3/2002 | Blach et al. |
| 6,533,412 | B1 | 3/2003 | Wang et al. |
| 6,540,349 | B1 | 4/2003 | Liesegang |
| 6,648,471 | B1 | 11/2003 | Dalrymple et al. |
| 6,676,681 | B1 | 1/2004 | Blach et al. |
| 6,823,864 | B2 | 11/2004 | Blach et al. |
| 7,091,634 | B2 | 8/2006 | Yi et al. |
| 7,118,210 | B2 | 10/2006 | Landers |
| 7,793,661 | B2 | 9/2010 | Macken |
| D639,762 | S | 6/2011 | Brogden et al. |
| D644,324 | S | 8/2011 | Brunner et al. |
| D644,325 | S | 8/2011 | Brunner et al. |
| 8,042,542 | B2 | 10/2011 | Ging et al. |
| 8,292,427 | B2 | 10/2012 | Zelazowski |
| 8,459,254 | B1 | 6/2013 | Jassir et al. |
| D696,400 | S | 12/2013 | Brogden et al. |
| D701,957 | S | 4/2014 | Brunner et al. |
| D703,318 | S | 4/2014 | Brunner et al. |
| 2002/0029408 | A1 | 3/2002 | Lindahl |
| 2003/0000521 | A1 | 1/2003 | Beaudry |
| 2007/0105824 | A1 | 5/2007 | Erickson-Miller et al. |
| 2007/0252946 | A1 | 11/2007 | Welchel |
| 2008/0097517 | A1 | 4/2008 | Holmes et al. |
| 2008/0119885 | A1 | 5/2008 | Yazdi |
| 2009/0183734 | A1 | 7/2009 | Kwok et al. |
| 2009/0188023 | A1 | 7/2009 | Hsu |
| 2010/0309425 | A1 | 12/2010 | Zelazowski |
| 2011/0000483 | A1 | 1/2011 | Matthias et al. |
| 2011/0230952 | A1 * | 9/2011 | Kassab ............ A61B 17/12113 623/1.11 |
| 2012/0024639 | A1 | 2/2012 | Castro |
| 2012/0036607 | A1 | 2/2012 | Beliveau |
| 2012/0172923 | A1 | 7/2012 | Fenton et al. |
| 2014/0296904 | A1 | 10/2014 | Andre |
| 2014/0375946 | A1 | 12/2014 | Rochford et al. |
| 2015/0001014 | A1 | 1/2015 | Noborio et al. |
| 2015/0173933 | A1 | 6/2015 | Castillo |
| 2015/0173934 | A1 | 6/2015 | Castillo |
| 2016/0193070 | A1 | 7/2016 | Castillo |
| 2017/0106222 | A1 | 4/2017 | Mayer et al. |

FOREIGN PATENT DOCUMENTS

| | | |
|---|---|---|
| JP | 2009-535079 | 10/2009 |
| KR | 200404740 | 12/2005 |
| WO | WO2002/003125 | 1/2002 |

OTHER PUBLICATIONS

International Search Report and Written Opinion for International Application No. PCT/US14/69817, dated Mar. 11, 2015, 11 pages.

International Search Report and Written Opinion of International Application No. PCT/US15/67530, dated May 16, 2016, 11 pages.

International Search Report and Written Opinion of International Application No. PCT/US2016/022637, dated Jun. 9, 2016, 10 pages.

Australian Government IP Australia, Examination report No. 1 for standard patent application, dated Oct. 24, 2017, 5 pages.

Office Action for corresponding Japanese Patent Application No. 2016-560622 with English translation, dated Nov. 1, 2017, 5 pages.

International Search Report and Written Opinion for International Application No. PCT/US 17/45688, dated Oct. 31, 2017, 11 pages.

European Patent Office, extended European search report for Application No. EP 14871764, dated Jul. 7, 2017, 10 pages.

Patent Cooperation Treaty, International Preliminary Report on Patentability for Application No. PCT/US16/22637, dated Aug. 3, 2017, 9 pages.

First Office Action of CN Application 201480075735.9, dated May 2, 2017, 9 pages.

Summary of First Office Action of CN Application 2014800757359, dated May 2, 2017, 5 pages.

Patent Cooperation Treaty, International Search Report and Written Opinion for International Application No. PCT/US2018/066312, dated Mar. 5, 2019, 12 pages.

* cited by examiner

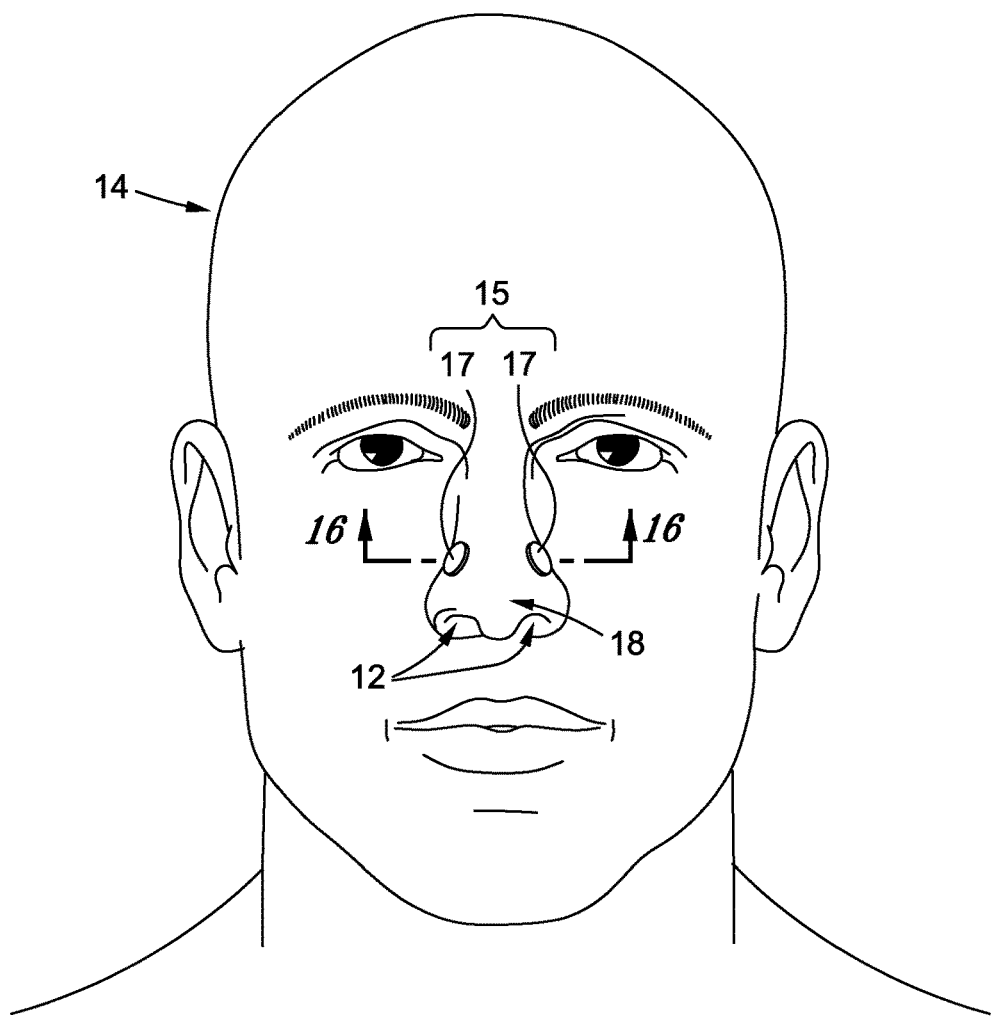
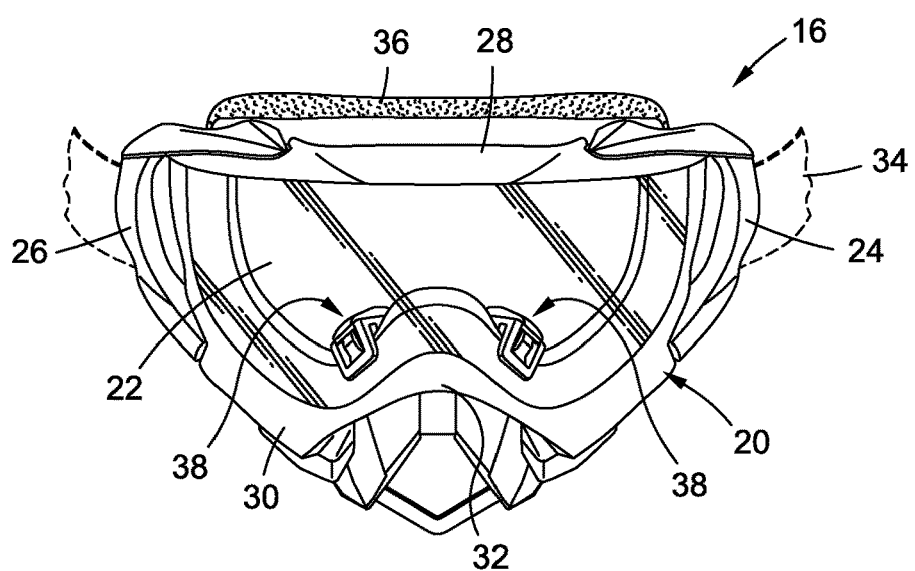
Fig. 1

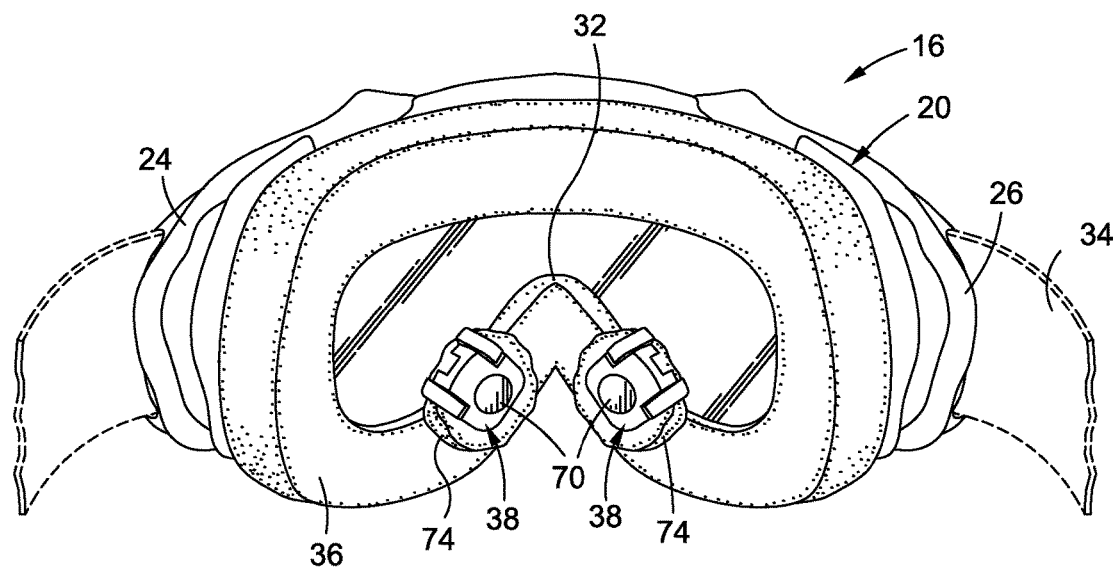
Fig. 2
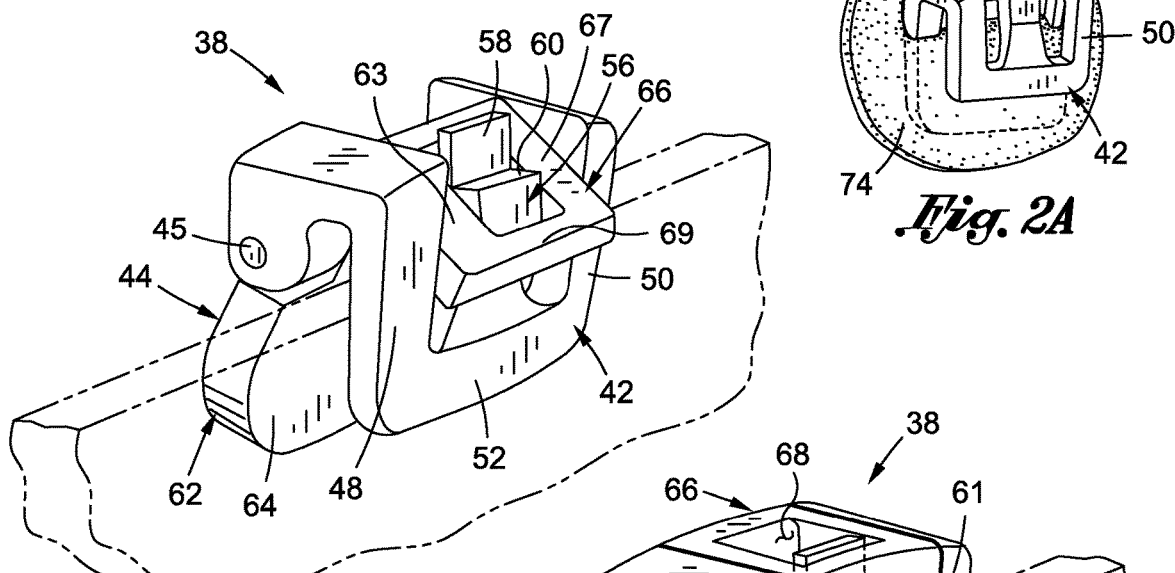
Fig. 2A
Fig. 3
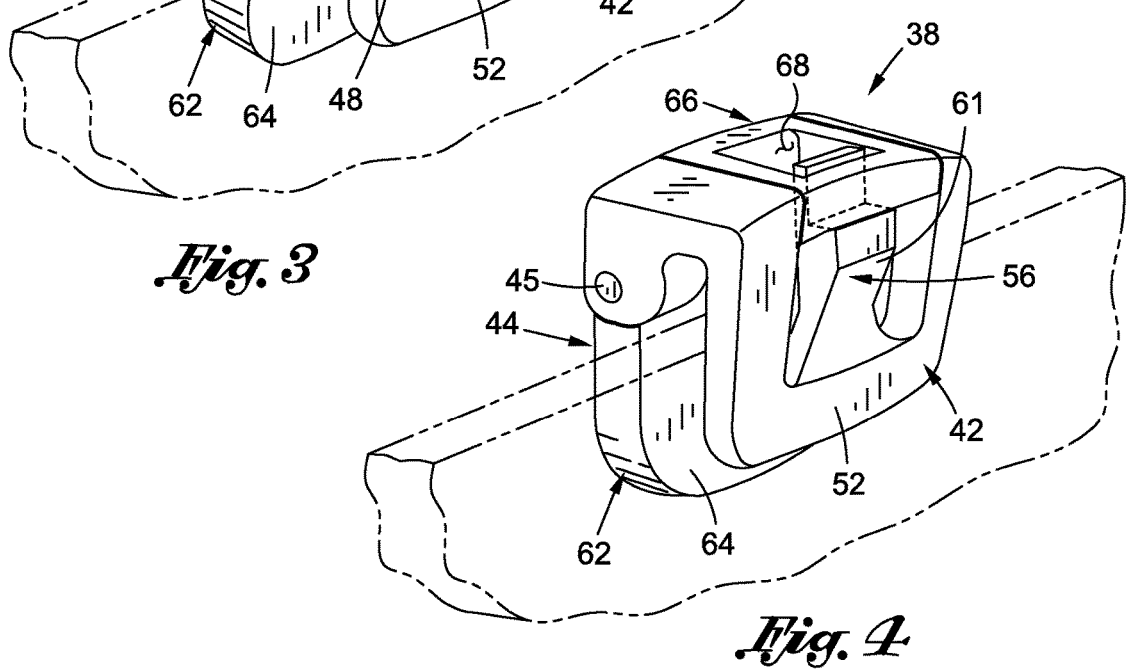
Fig. 4

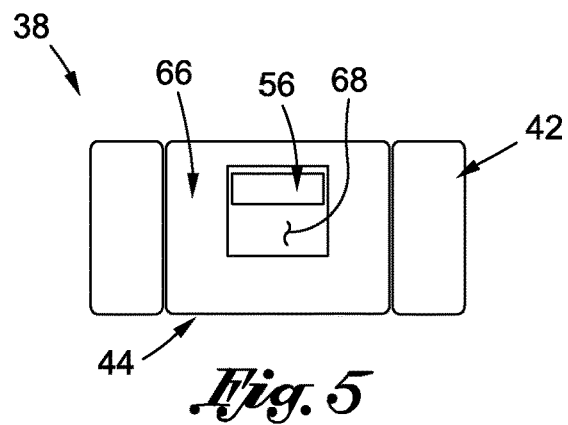
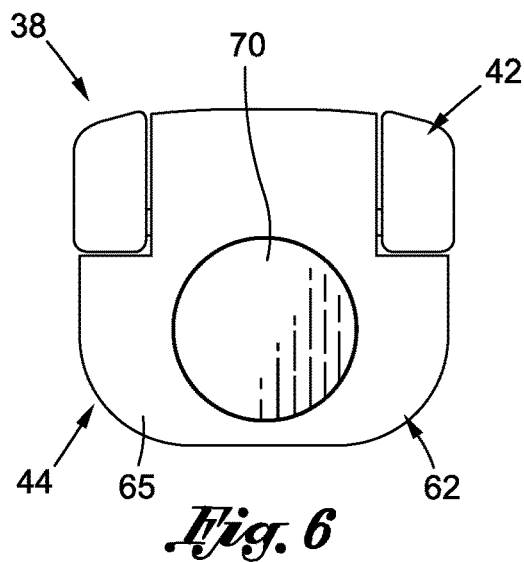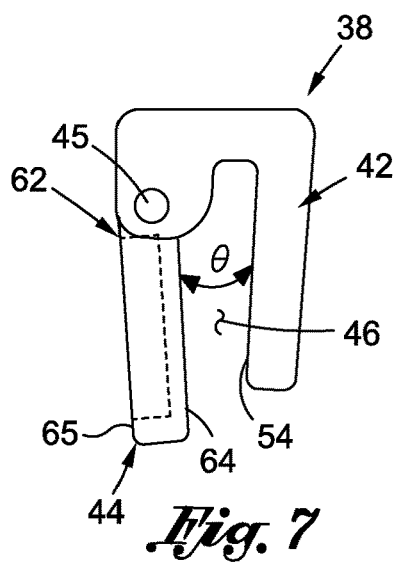
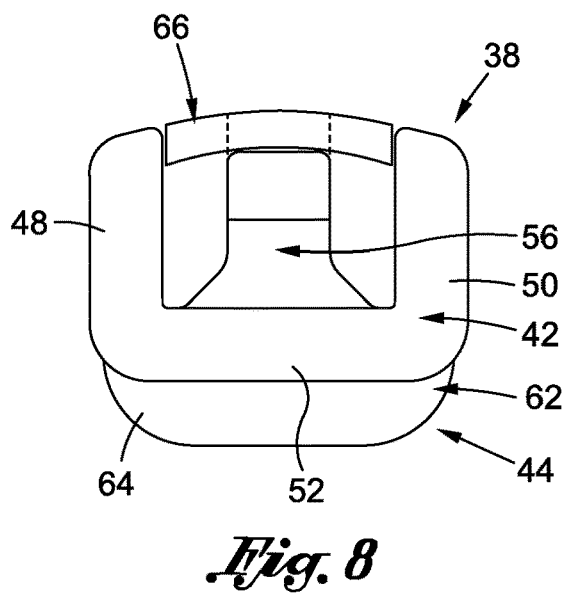

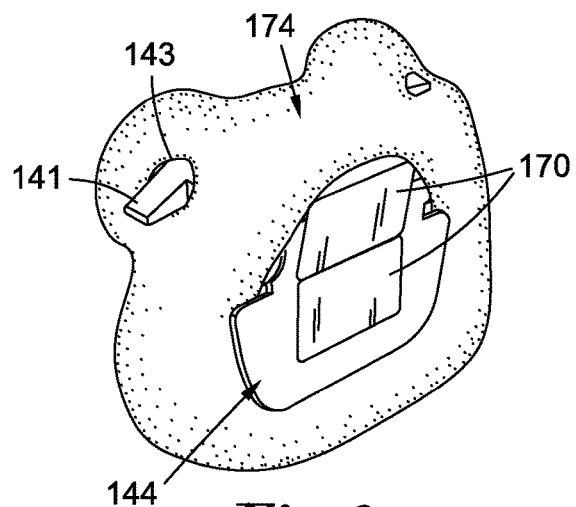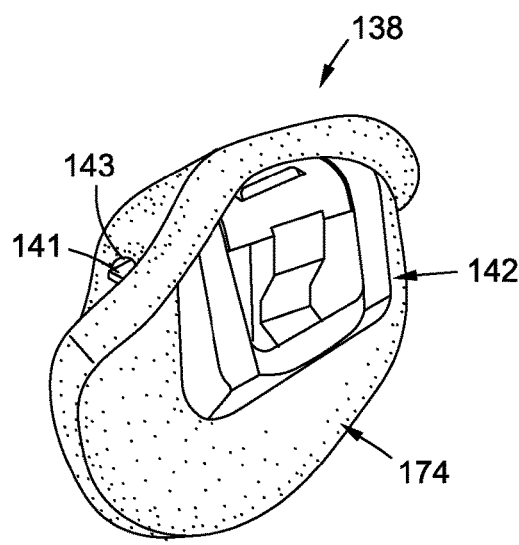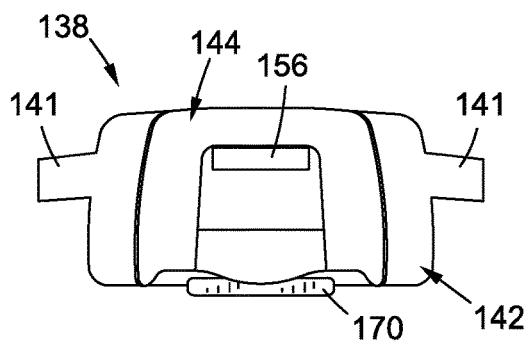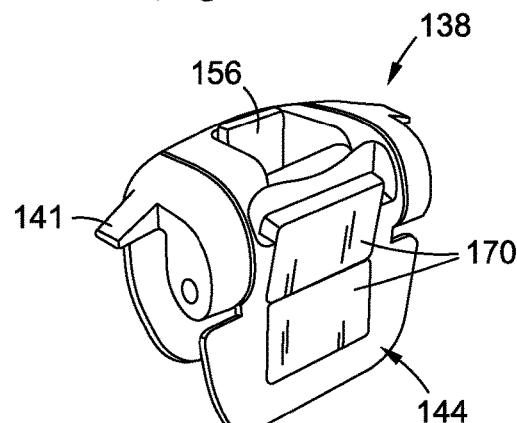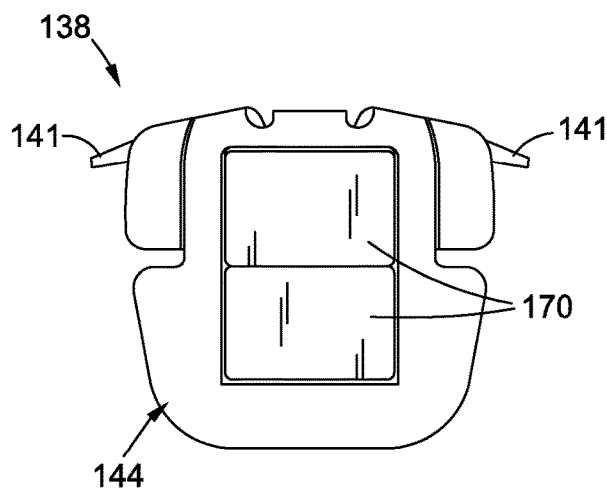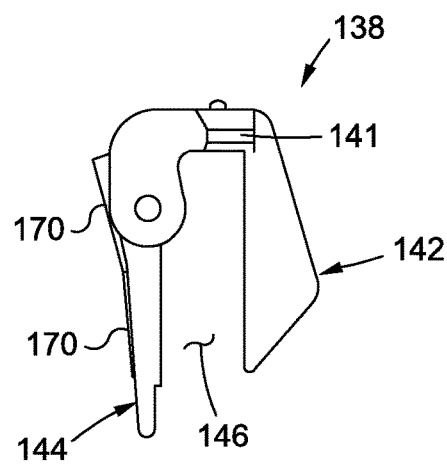

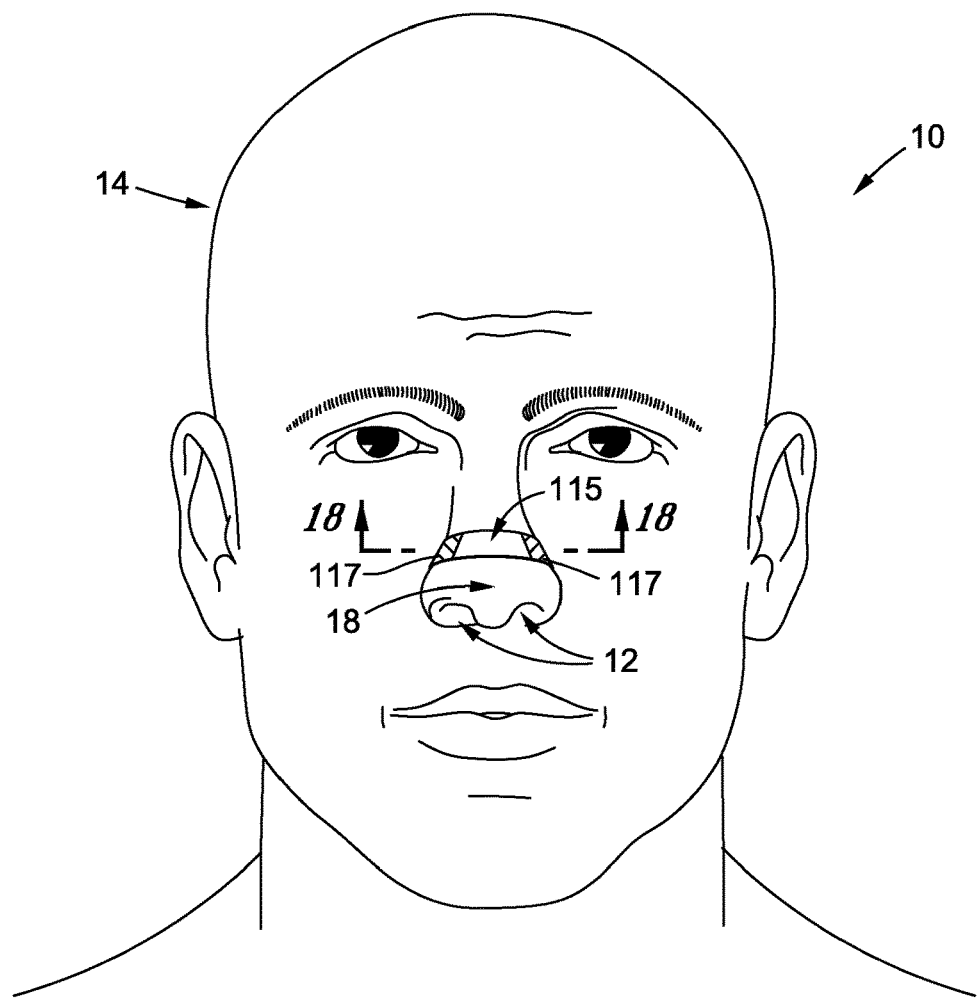
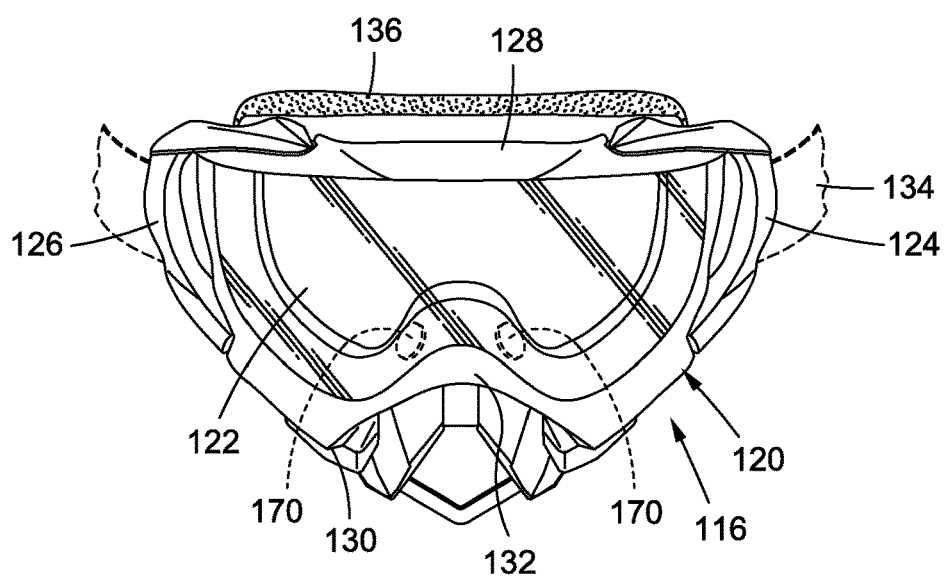
Fig. 17

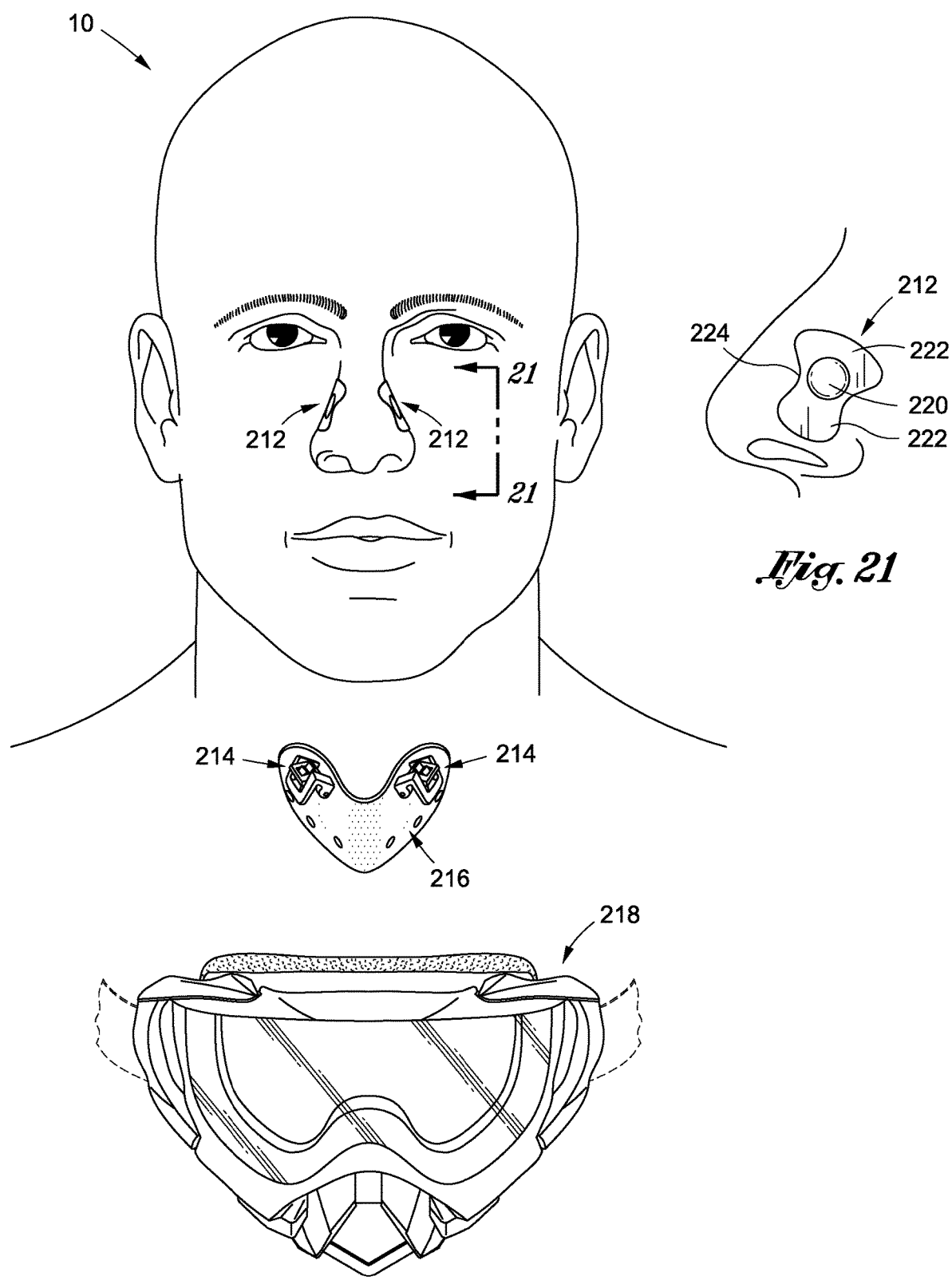

GOOGLE BREATHING SYSTEM

CROSS-REFERENCE TO RELATED APPLICATIONS

This application is a continuation-in-part of U.S. patent application Ser. No. 14/622,448, filed Feb. 13, 2015, which is a continuation-in-part of U.S. patent application Ser. No. 14/502,348, filed Sep. 30, 2014, which claims the benefit of U.S. Provisional Application No. 61/918,826, filed Dec. 20, 2013, and U.S. Provisional Application No. 61/937,018, filed Feb. 7, 2014, the contents of each of the foregoing applications being expressly incorporated herein by reference.

STATEMENT RE: FEDERALLY SPONSORED RESEARCH/DEVELOPMENT

Not Applicable

BACKGROUND OF THE INVENTION

1. Field of the Invention

The present invention relates generally to a breathing enhancement system, and more specifically to a breathing enhancement system including a nasal applique wearable on a user's nose and adapted for use with eyewear to dilate the user's nose when the eyewear is worn by the user.

2. Description of the Related Art

It is readily understood that breathing is important when playing sports or taking part in physical competition due to the increased demand for oxygen by the body. Breathing may be achieved by drawing air into the body through an individual's nostrils and/or through the individual's mouth. However, in some instances, it is preferable to breathe almost exclusively through the nostrils, as there may be a downside to breathing through one's mouth. Along these lines, breathing through the mouth may lead to rapid water loss and heat loss, both of which increase the likelihood of exercise-induced asthma.

It is also understood that eyewear is commonly used when participating in many sports and activities. Such eyewear may include protective eyewear, or vision-enhancing (e.g., prescription) eyewear. For instance, goggles are readily worn by many athletes participating in snowboarding, skiing, motocross, automotive racing, basketball, baseball, hockey, etc. Goggles are typically configured such that a portion of the goggle frame extends over the wearer's nose, and thus, goggles may impact one's ability to breathe through the wearer's nasal passage.

Moreover, many goggles are fitted with a foam liner which interfaces with the wearer's face to create a barrier or seal which prevents snow, rain, dirt or other debris from entering the goggles and creating a potential irritant in the wearer's eye. In order to create an effective seal or barrier around the goggles, the goggles are compressed against the wearer's face, typically through the use of an elastic band which is worn around the head. The compression of the foam liner against the wearer tends to compress the nasal passages of the wearer, which further inhibits the ability of the wearer to breathe through the nose.

Accordingly, there is a need in the art for a device which can be used with a goggle or other eyewear for enhancing the wearer's ability to breathe through the wearer's nasal passage. Various aspects of the present invention address this particular need, as will be discussed in more detail below.

BRIEF SUMMARY OF THE INVENTION

In accordance with one embodiment of the present invention, there is provided a goggle kit including a goggle clip attachable to the goggle frame, and a corresponding nose element (e.g., applique), which adheres to the wearer's nose. The goggle clip attaches to the goggle frame to compress the foam liner to create space for the nose element to enable the nose element to move outward toward the clip. The nose element and the goggle clip are configured to be attachable to each other, such that the nose element is moved in an outward direction and/or forward direction to engage with the clip. The outward and/or forward movement of the nose element causes the nasal opening of the wearer to dilate. Therefore, even though the wearer is using goggles, the wearer can breathe more freely through his or her nasal passageway.

The goggle clip may include a pair of clip members which are transitional between an extended position and a clamping position for securing the goggle clip to the goggle frame. The clip members may move toward each other as the clip transitions from the extended position toward the clamping position. The goggle clip may include a spring clip, or may include a hinge to allow the clip to transition between the extended and clamping positions.

The nose element may include a pair of nose pieces positionable over respective ones of the user's nostrils. The nose element may also include a single strip which is extendable over the user's nose between the user's nostrils. The nose element may include an adhesive for temporarily securing the nose element to the user.

Engagement between the goggle clip and the nose element may be by way of magnetic attraction, hook and loop fasteners (e.g., VELCRO), adhesives, snaps, clips, friction, or other mechanical engagement mechanisms known in the art.

According to one embodiment, there is provided an eyewear system adapted to open a nasal passage of a user. The eyewear system includes a wearable frame having a bridge section configured to be placeable adjacent the nose of the user. A nasal attachment member is configured to be selectively placeable on the nose of the user adjacent the nasal passage. The nasal attachment member is adapted to be urged toward the wearable frame in response to placement of the wearable frame adjacent the nose of the user to cause the nasal passage of the user to open.

The system may include a liner coupled to the wearable frame and configured to interface with the user when the wearable frame is placed on the user. The liner may be formed from a compressible material. The system may additionally include a clip configured to be selectively attachable to the wearable frame and adapted to urge the nasal attachment member toward the wearable frame in response to placement of the wearable frame adjacent the nose of the user. A peripheral barrier member may be coupled to the clip and configured to interface with the user to mitigate the passage of particulate between the wearable frame and the user when the clip is attached to the wearable frame and the wearable frame is placed adjacent the nose of the user.

The clip may include a first clip member and a second clip member pivotally coupled to the first clip member. The first clip member may be pivotable relative to the second clip member between an open position and a closed position. An angle between the first and second clip members may decrease as the first and second clip members pivot from the open position toward the closed position. The first and second clip members may be configured to become locked when the first and second slip members are in the closed position.

The nasal attachment member may be configured to be magnetically urged toward the wearable frame. The system may include a frame magnet coupled to the wearable frame and magnetically attractable to the nasal attachment member.

According to another embodiment, there is provided a method of enhancing a nasal airway of a user wearing goggles having a compressible barrier member. The method includes compressing the compressible barrier member on the goggles to form a recess within the barrier member, attaching a nasal attachment member to the user adjacent the user's nostrils, and placing the goggles on the wearer after the compressible barrier member has been compressed, placement of the goggles on the wearer urges the nasal attachment member to move into the recess formed within the barrier member, movement of the nasal attachment member into the recess causes the nasal airway of the user to dilate.

According to yet another embodiment, there is provided a disposable apparatus attachable to a nose of a wearer and configured for use with an external magnetic element positioned adjacent to the nose of the wearer. The disposable apparatus includes a flexible base layer including a first surface and an opposing second surface, and an adhesive disposed on the first surface of the flexible base layer and configured to produce an adhesive force between the flexible base layer and the wearer for attaching the flexible base layer to the nose of the wearer. The adhesive is configured to increase the adhesive force after the flexible base layer has been attached to the nose of the wearer. A metallic element is coupled to the second surface of the base layer and is configured to magnetically interact with the magnetic element when the magnetic element is positioned adjacent the nose of the wearer and the flexible base layer is attached to the nose of the wearer, with the magnetic interaction between the metallic element and the magnetic element imparting a dilating force on the nose of the wearer causing the nose of the wearer to dilate.

The adhesive may be adapted to increase the adhesive force after the flexible base layer has been attached to the nose of the wearer for a prescribed residency period. The adhesive may include at least one of polyethylene tape and polyolefin tape.

The metallic element may include a metallic powder.

According to yet another embodiment, there is provided a breathing enhancement system for use with eyewear having a compressible liner. The breathing enhancement system includes a pair of clips configured to be selectively attachable to the eyewear and adapted to compress the compressible liner when attached to the eyewear to define a compressed portion of the compressible liner. A clip liner is adapted to engage with and extend between the pair of clips, with the clip liner being configured to reside within the compressed portion of the compressible liner. A pair of nasal appliques are configured to be selectively placeable on respective lateral portions the nose of a user, with each nasal applique being adapted to be magnetically urged toward a respective one of the pair of clips in response to placement of the eyewear adjacent the nose of the user to cause the nasal passage of the user to open.

The present invention will be best understood by reference to the following detailed description when read in conjunction with the accompanying drawings.

BRIEF DESCRIPTION OF THE DRAWINGS

These and other features and advantages of the various embodiments disclosed herein will be better understood with respect to the following description and drawings, in which:

FIG. 1 is a front view of a user wearing a pair of nasal elements and goggles having clips attached thereto which cooperate with the nasal elements to open the nasal passage;

FIG. 2 is rear perspective view of the goggles and clips depicted in FIG. 1;

FIG. 2A is an upper perspective view of the clip shown in FIG. 2 having a barrier member attached thereto;

FIG. 3 is a perspective view of the clip shown in FIG. 2 with the foam liner removed, wherein the clip is in an open position;

FIG. 4 is a perspective view of the clip shown in FIG. 3, wherein the clip is in the closed position;

FIG. 5 is a top view of the clip shown in FIG. 3, wherein the clip is in the closed position;

FIG. 6 is a front view of the clip shown in FIG. 3, wherein the clip is in the closed position;

FIG. 7 is a side view of the clip shown in FIG. 3, wherein the clip is in the closed position;

FIG. 8 is a rear view of the clip shown in FIG. 3, wherein the clip is in the closed position;

FIG. 9 is a front upper perspective view of a second embodiment of a clip having a foam liner and a pair of magnets;

FIG. 10 is a rear upper perspective view of the clip shown in FIG. 9, wherein an end portion of the foam liner has been moved relative to its position shown in FIG. 9;

FIG. 11 is a top view of the clip shown in FIG. 9;

FIG. 12 is an upper perspective view of the clip depicted in FIG. 9;

FIG. 13 is a front view of the clip depicted in FIG. 9;

FIG. 14 is a side view of the clip depicted in FIG. 9;

FIG. 17 is a front view of a user wearing a nasal strip and goggles having embedded magnets which urge the nasal strip toward the goggles to open the user's nasal passage when the goggles are worn;

FIG. 20 is a front view of another embodiment of a breathing enhancement system;

FIG. 21 is a side view of a user's nose having a nasal applique of the breathing enhancement system shown in FIG. 20 applied to the user's nose;

Common reference numerals are used throughout the drawings and the detailed description to indicate the same elements.

DETAILED DESCRIPTION OF THE INVENTION

Figure 15:
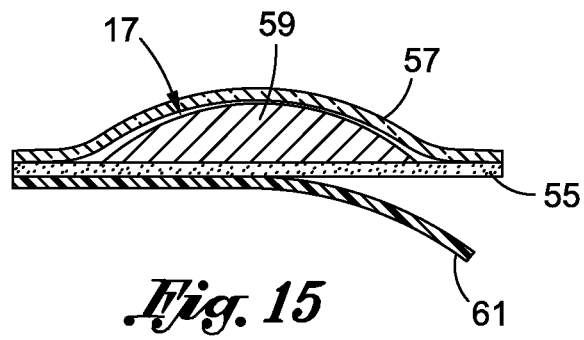
FIG. 15 is a side sectional view of a nose element having a peel-away liner partially removed therefrom.

The detailed description set forth below in connection with the appended drawings is intended as a description of certain embodiments of a goggle breathing system and is not intended to represent the only forms that may be developed or utilized. The description sets forth the various structure and/or functions in connection with the illustrated embodiments, but it is to be understood, however, that the same or equivalent structure and/or functions may be accomplished by different embodiments that are also intended to be encompassed within the scope of the present disclosure. It is further understood that the use of relational terms such as first and second, and the like are used solely to distinguish one entity from another without necessarily requiring or implying any actual such relationship or order between such entities.

Referring now to the drawings, wherein the showings are for purposes of illustrating a preferred embodiment of the present invention only, and are not for purposes of limiting the same, there is depicted a system 10 configured to open or dilate the nasal passages 12 of an individual 14 wearing eyewear, such a goggles 16. The system 10 generally includes a nasal attachment member 15 including a pair of nasal elements (e.g., nasal appliques) 17 which are worn by the wearer 14 adjacent the wearer's nostrils. The system 10 is configured such that when the goggles 16 are placed on the wearer 14, the nasal attachment member 15 is urged toward the goggle frame 20, which results in dilation of the nasal opening, thereby making it easier for the wearer 14 to breathe, despite the existence of the goggles 16 extending over the wearer's nose 18.

Referring now specifically to FIG. 1, there is depicted a set of goggles 16 having a wearable frame 20 including a frame opening, within which is positioned a lens 22. The frame 20 includes opposed lateral end portions 24, 26, a top portion 28, and an opposing bottom portion 30 having a bridge section 32 which fits over the nose 18 of the wearer 14. The frame 20 may be fabricated from plastic, rubber, or other materials known by those skilled in the art. A headband or strap 34 may be connected to the opposed lateral end portions 24, 26 of the frame 20 for securing the frame 20 to the wearer's head.

Although the exemplary embodiment shows the wearable frame 20 as being a frame for goggles 16, it is understood that the term wearable frame may broadly refer to other eyewear frames which may be worn by a wearer, such as frames associated with various helmet systems and the like.

A foam liner 36 extends around an inner peripheral portion of the frame 20 and rests against the wearer's head when the goggles 16 are worn by the wearer 14. The foam liner 36 is designed to interface with the wearer's face to create a seal or barrier around the frame 20 so as to prevent unwanted debris or particulate from passing between the goggles 16 and the wearer 14 so as to protect the wearer's eyes. The liner 36 is preferably formed of a breathable material so as to allow air to pass therethrough to allow for ventilation within the goggles 16.

It is understood that goggles 16 come in various shapes, sizes and configurations depending on the particular size of the wearer 14, as well as the intended use of the goggles 16. Consequently, the term "goggles" refers broadly to any eyewear that is worn while snowboarding, snow skiing, motorcycle racing (e.g. motocross), automobile racing, or playing a wide variety of sports such as basketball, baseball, football, hockey, etc., for the purpose of protecting the wearer's eyes, or for providing enhanced visibility.

One embodiment of system 10 additionally includes a goggle attachment member or clip(s) 38, which may be selectively and securely attached to the frame 20 of the goggle 16. Each clip 38 is specifically adapted to engage with a corresponding nasal element 17 through complimentary fastening members. The engagement between the clip 38 and the nasal element 17 causes dilation of the nasal passageways, as will be described in more detail below. When the clip 38 is attached to the goggle 16, the clip 38 compresses the liner 36 to create space around the wearer's nose 18 to allow the nasal element 17 to be drawn outwardly and forwardly thereby causing the nose 18 to dilate.

According to one embodiment, and referring now specifically to FIGS. 2-8, a first embodiment of a clip 38 is shown, which includes a first clip member 42 and a second clip member 44 pivotally connected to the first clip member 42 via a hinge 45. The first and second clip members 42, 44 form opposing locking tabs defining a clip channel 46 (see FIG. 7) therebetween sized and adapted to receive a portion of the goggle frame 20 to allow the clip 38 to clamp onto the goggle frame 20.

As shown in FIGS. 3-8, the first clip member 42 includes a pair of opposing lateral arms 48, 50 which are interconnected by a connecting arm 52. The opposing lateral arms 48, 50 and the connecting arm 52 collectively define a first clamping surface 54 (see FIG. 7), which faces the clip channel 46. The first clip member 42 further includes a locking arm 56 extending from the connecting arm 52, wherein the locking arm 56 includes a first locking surface 58 (see FIG. 3), a second locking surface 60, and an outer cam surface 61, the purposes of which will be described in more detail below.

The second clip member 44 includes a primary wall 62 having a second clamping surface 64 facing the clip channel 46 in opposed relation to the first clamping surface 54 of the first clip member 42. The first and second clamping surfaces 54, 64 define an angle Θ (see FIG. 7) therebetween. The second clip member 44 further includes an outer surface 65 (see FIG. 7) opposite the second clamping surface 64. A secondary wall 66 extends from the primary wall 62 and includes a pair of lateral arms 63, 67, and a distal arm 69 extending between the lateral arms 63, 67. An opening 68 is formed within the secondary wall 66, wherein the opening 68 is sized and adapted to receive the locking arm 56 of the first clip member 42.

The first clip member 42 is adapted to be selectively transitional relative to the second clip member 44 between an open position and a closed position. In particular, the angle Θ between the first clamping surface 54 and the second clamping surface 64 decreases when the first and second clip members 42, 44 transition from the open position toward the closed position. Conversely, the angle Θ between the first clamping surface 54 and the second clamping surface 64 increases when the first and second clip members 42, 44 transition from the closed position toward the open position.

When the clip 38 is in the open position (see FIG. 3), the locking arm 56 of the first clip member 42 extends through the opening 68 formed in the secondary wall 66 of the second clip member 44. Furthermore, the distal arm 69 rests against the outer cam surface 61, which prevents the clip 38 from freely moving from the open position toward the closed position. For the clip 38 to be transitioned from the open position toward the closed position, the user presses the first clip member 42 toward the second clip member 44. This causes the locking arm 56 to flex, which in turn, allows the distal arm 69 to move along the locking arm 56 toward the locking surfaces 58, 60, and the locking arm 56 to retract through the opening 68 until a portion of the secondary wall 66 interfaces with the first and second locking surfaces 58, 60 of the locking arm 56. Once the clip 38 is in the closed position, the engagement between the secondary wall 66 and the locking arm 56, specifically, the second locking surface 60, prevents the clip 38 from moving from the closed position toward the open position. Therefore, the clip 38 may be adapted to prevent free movement between the open position and the closed position.

In order to move the clip 38 from the closed position toward the open position, the locking arm 56 is disengaged from the secondary wall 66, typically by pressing the locking arm 56 toward the primary wall 62 of the second clip member 44 until the locking arm 56 can be advanced through the opening 68. In this respect, the first clip member 42 is constructed from a material having suitable flexibility to enable flexing of the locking arm 56 relative to the connecting arm 52.

One or more magnets 70 is connected to the clip 38 at an engagement region of the clip 38. The magnet 70 is nested within a cavity extending into the clip 38 from the outer surface 65. The magnet 70 and the cavity within which the magnet 70 is nested are preferably configured such that the outer surface of the magnet 70 is substantially flush with the outer surface 65 of the second clip member 44 when the magnet 70 is nested within the cavity. The magnet 70 is adapted to magnetically urge the nasal attachment member 15 worn by the wearer 14 toward the goggle frame 20 for purposes of opening or dilating the nasal passages of the wearer 14.

According to one embodiment, the magnet 70 is a neodymium, N42 grade magnet, although magnets of differing grades or materials may also be used without departing from the spirit and scope of the present invention. Furthermore, the size of the magnet 70 may range from approximately 0.25"-0.75" in diameter. For instance, the magnet 70 may be ⅜" or ½" in diameter, although other sizes and shapes may also be used.

When the clip 38 is placed on the goggle frame 20, the clip 38 compresses the foam 36 lining the inner perimeter of the goggle 16 to create a cavity. This cavity creates space within the liner 36 adjacent the wearer's nostril to allow the nasal element 17 to move outwardly causing the nostril to dilate. However, compressing the foam 36 on the goggle 16 may compromise the seal or barrier around the goggle 16 and allow rain, snow, dirt or other particulate to enter the goggle 16 and interfere with the wearer's vision. Therefore, according to one embodiment, and referring now to FIGS. 2 and 2A, a peripheral foam liner 74 is coupled to the clip 38 and is compressed against the foam 36 on the goggle 16 when the nasal element 17 is magnetically drawn to the clip 38, as described in more detail below, so as to effectively form a peripheral barrier member around the clip 38. The clip liner 74 and goggle liner 36 cooperate with each other to prevent particulate from entering the goggles 16, even though the clip 38 has compressed the foam 36 on the goggle 16. Furthermore, the foam-against-foam arrangement between the clip liner 74 and goggle liner 36 adds to grip between the clip 38 and the goggle 16. The peripheral foam liner 74 is preferably configured to enable air to pass therethrough to allow for ventilation.

FIG. 2 shows two clips 38 attached to the goggle 16 in spaced relation to each other, wherein each clip 38 includes its own peripheral foam liner 74. In another embodiment, the pair of clips 38 includes a common foam liner (see FIGS. 20, 22-24, and 27-28) which includes a bridge section that extends over the nose. When the pair of clips 38 having a common foam liner is used, it causes the goggle 16 to set slightly farther from the nose, creating more of a gap, which increases the space between the magnetic member and the user's nose allowing for greater dilation of the nose.

Referring now specifically to FIGS. 9-14, there is depicted a second embodiment of a clip 138. The primary distinction between the second embodiment of the clip 138 and the first embodiment of the clip 38 is that the second embodiment of the clip 138 includes a pair of magnets 170 coupled thereto, as well as attachment arms 141 for securing the foam liner 174 to the clip 138. The basic structural attributes of the second embodiment of the clip 138 are similar to the basic structural attributes of the first embodiment of the clip 38. In particular, the clip 138 includes a first clip member 142 and a second clip member 144 pivotally connected to the first clip member 142 via a hinge 145. The first and second clip members 142, 144 form opposing locking tabs defining a clip channel 146 (see FIG. 14) therebetween, wherein the clip channel 146 is sized and adapted to receive a portion of the goggle frame 20 to allow the clip 138 to clamp onto the frame 20. The clip 138 further includes a locking arm 156 which operates in a manner similar to the locking arm 56 of the clip 38.

As noted above, the clip 138 includes a pair of attachment arms 141 extending laterally outward from the first clip member 142. The attachment arms 141 are adapted to extend through corresponding openings 143 formed in the foam liner 174 to secure the foam liner 174 to the clip 138. In this respect, the clip 138 and liner 174 are configured to enable selective removal of the liner 174 from the clip. As such, liners 174 with different thicknesses may be used to accommodate different types of foam liners on different goggles.

Two magnets 170 are connected to the clip 138 to enhance the magnetic attraction, compared to just a single magnet. The magnets 170 may be arranged in a side-by-side configuration, wherein the magnetic poles of the magnets 170 are opposite to each other. The external engagement surfaces of the magnets 70 may be slightly offset from each other to define a generally concave configuration to enhance engagement with a corresponding "domed" or arcuately shaped metallic nasal elements.

Figure 16:
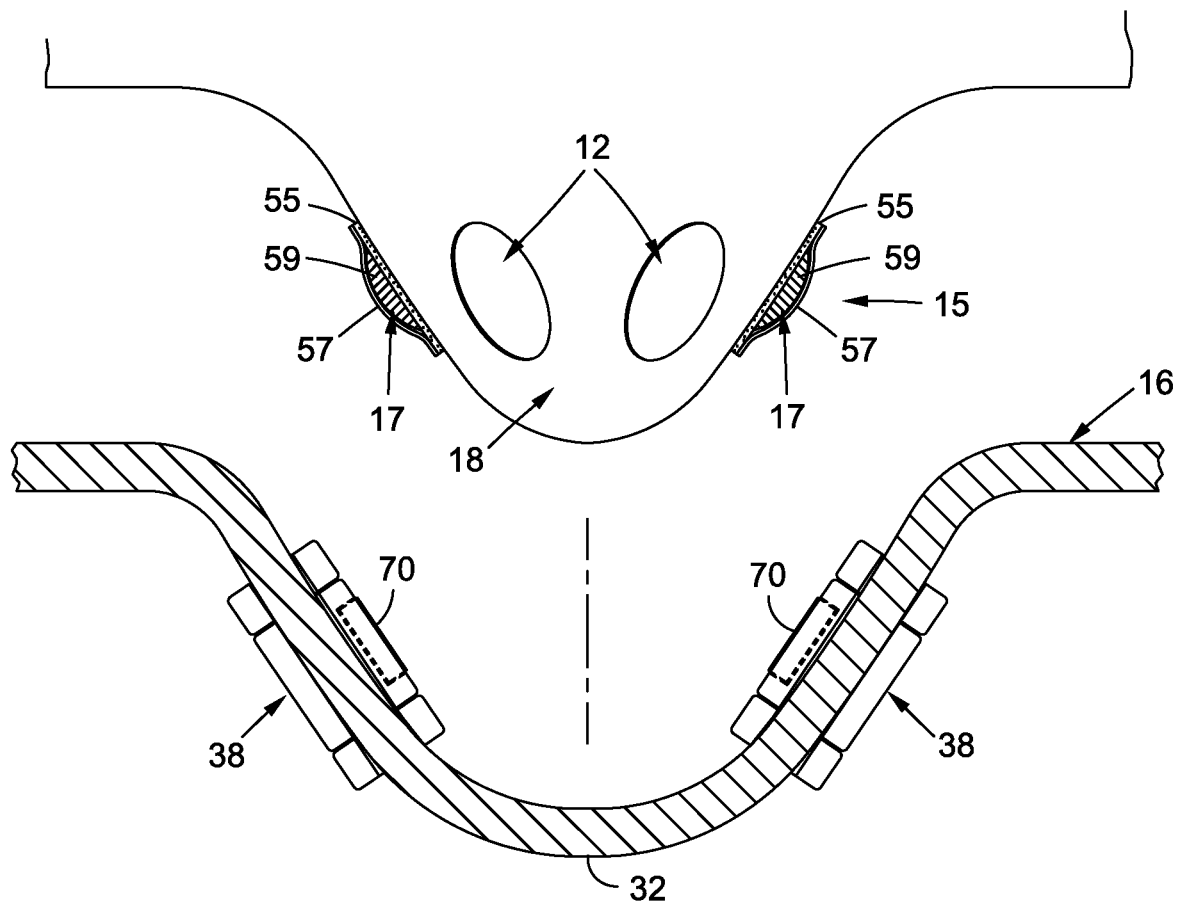
FIG. 16 is a bottom view of the goggle being brought into alignment with the wearer and nasal elements worn by the wearer.

Each nasal element (e.g., nasal applique) 17 may be secured to the wearer's nose 18 via an adhesive layer 55 located on the underside of the nasal element 17. The use of separate nasal elements 17 allows the user to pinpoint the exact location of each nasal element 17 on the user. Each nasal element 17 may be configured for a one-time use and thus several nasal elements 17 may be packaged and sold as a set. Referring now to FIG. 15-16, there is depicted a cross sectional view of a nasal element 17, which includes a base layer 55 and an outer layer 57 which collectively encapsulate a magnetically attractable element 59, such as a ferrous material (e.g., a metallic element).

According to one embodiment, the metallic element 59 is preferably located in a generally central location relative to the underlying base layer 55. Such central positioning causes the central portion of the base layer 55 to be pulled toward the magnetic element 59 when the magnetic element 70 is placed adjacent the metallic element 59. The centrally applied force on the base layer 55 creates a shear force between the base layer 55 and the user's nose 10. In this respect, although the magnetic attraction between the magnet 70 and the metallic element 59 pulls the metallic element 59 along an axis extending between the magnet 70 and the metallic element 59, the generally central location of the metallic element 59 relative to the base layer 55 distributes a portion of the force created by the attraction of the metallic element 59 and the magnets 70 to the compliant area around the metallic element 59 which substantially translates the force to shear in a plane along the skin of the user's nose, which is generally offset from the axis extending between the magnet 70 and the metallic element 59, and in some instances, may be perpendicular to such axis. The shear component allows for a much more aggressive dilation compared to systems that pull generally perpendicularly to the skin, as the adhesives are much stronger in shear.

One or more surfaces of the metallic element 59 may define an arcuate or "domed" configuration to allow contact between the magnet 70 and the nasal element 17 without flat-to-flat attachment which may create uncomfortable torque on the nostril. The base layer 55 may include a peel-off liner 61 which may be removed to expose adhesive for securing the nasal element 17 to the user's nose 18. The peel-off liner 61 may include a single continuous strip or a segmented strip. The exposed surface of the outer layer 57 may be imprinted with indicia or logos associated with the goggle manufacturer, clip manufacturer, athlete/team sponsor(s)/advertiser(s), nasal strip manufacturer, sports team, school, the wearer's initials, etc.

Although the foregoing describes the nasal element 17 as being attached to the wearer via an adhesive, it is also contemplated that nasal element 17 may be coupled to the wearer via piercings. It is also contemplated that the nasal element 17 may be coupled to the wearer via a clip which clamps onto the wearer's nose by having one portion that is inserted inside the nostril, and another portion which extends outside the nostril. In this respect, it is understood that any means may be used to attach the nasal element 17 to the wearer to position the nasal element 17 for magnetic coupling to the goggle.

With the basic structural features of one embodiment of the system 10 described above, operation of the system 10 will now be described. Prior to placing the goggles 16 on the wearer's head, the wearer 14 places the nasal elements 17 on his nose 18 such adjacent the wearer's nostrils (see FIGS. 1 and 16). The nasal elements 17 may have a protective lining covering an adhesive layer, and thus, the wearer 14 may have to peel the protective lining away from each nasal element 17 to expose the adhesive layer. When the adhesive layer is exposed, the wearer presses the nasal element 17 against the wearer's nose 18 to couple the nasal element 17 to the nose 18.

The wearer 14 also attaches the clips 38 to the goggle frame 20 adjacent the bridge section 32 of the frame 20. In particular, the clips 38 are positioned on opposed sides of a bridge apex, such that each clip 38 will be positioned adjacent a respective one of the wearer's nostrils when the goggles 16 are placed on the wearer 14. The clips 38 are attached to the goggle frame 20 from transitioning the clip 38 from the open position toward the closed position, as described in more detail above. When the clips 38 are attached to the goggle frame 20, each clip 38 forms a recess or depression within the foam liner 36 on the goggle 16.

With the nasal element 17 attached to the wearer 14 and the goggle clip 38 attached to the goggles 16, the wearer 14 places the goggles 16 on the wearer's head. Referring now specifically to FIG. 16, as the goggles 16 move toward the wearer's head, the clips 38 move closer to the nasal element 17, thereby causing the magnetic attraction between the clip magnet 70 and the ferrous body 59 to become stronger. When the goggles 16 are placed in their final position, the clip 38 acts as a "perch" or "locator" for the nasal element 17, such that the ferrous body 59 is drawn to a predetermined fixed distance into magnetic engagement with the clip magnets 70, which in turn causes the nasal passages 12 of the user to dilate. In particular, the nasal elements 17 are displaced outward and forward relative to their previous position to dilate the user's nose 18. The dilated nasal passage 12 allows the wearer 14 to breathe easier during physical activity so as to maintain elevated oxygen levels in the body.

Although the foregoing describes the nasal elements 17 and clip 38 as being engageable with magnets 70, it is also contemplated that other connectors may be used to connect the nasal elements 17 to the clip 38 without departing from the spirit and scope of the present invention. For instance, the engagement between the nasal element 17 and the goggle clip 38 may be by way of hook and loop fasteners, magnets, adhesives, or other engagement mechanisms known in the art.

Furthermore, although the embodiment of the clip 38 described above includes separate first and second clip members 42, 44 which are pivotally connected to each other, it is understood that other embodiments of the clip 38 may be used without departing from the spirit and scope of the present invention. Along these lines, the clip 38 may include a single, unitary body having a pair of opposed tabs which are flexible to enable placement of the clip onto the goggle frame 20.

Figure 18:
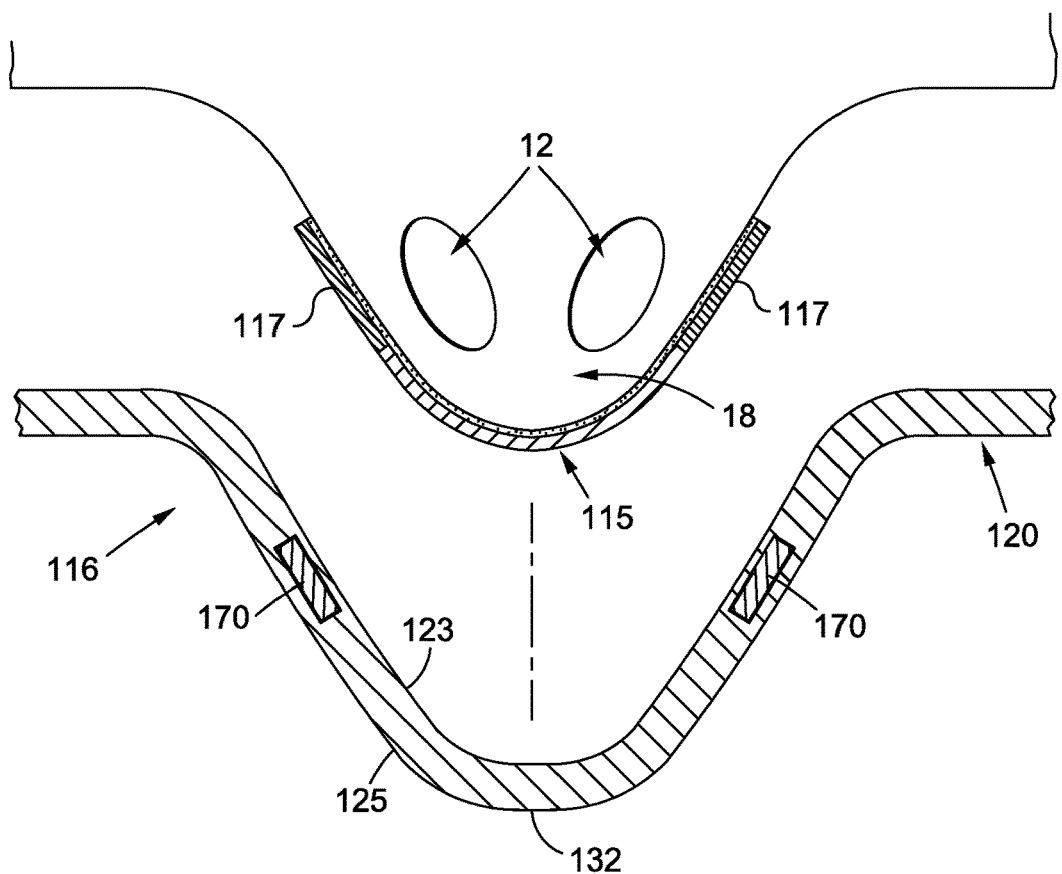
FIG. 18 is a bottom view of the goggles and clips being brought into alignment with the wearer and the nasal strip.
Figure 19:
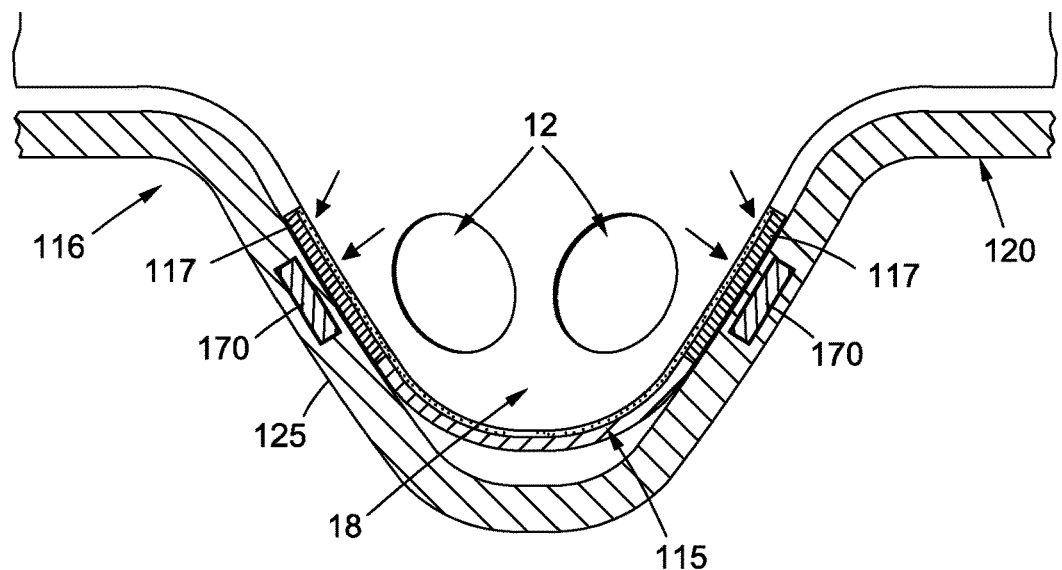
FIG. 19 is a bottom view of the goggles and the clips urging the nasal strip toward the goggle frame to open the wearer's nasal passage.
Figure 22:
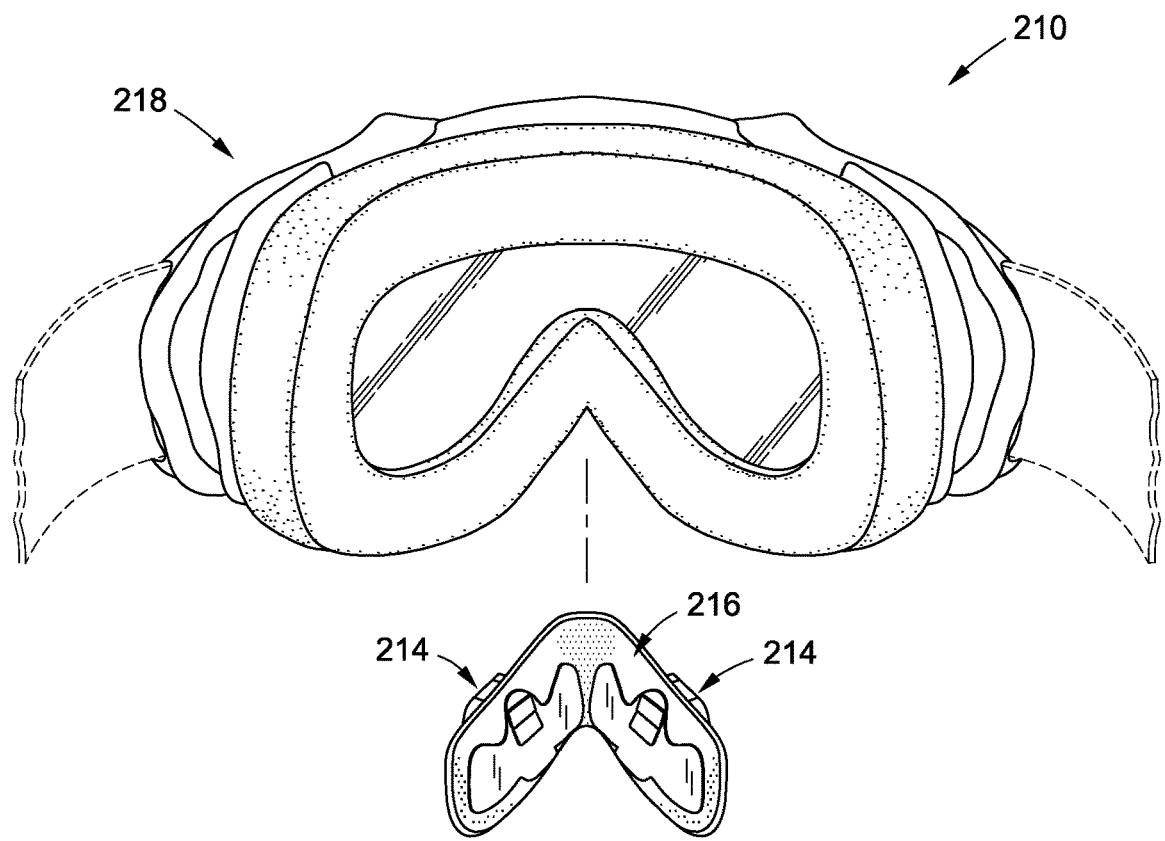
FIG. 22 is an exploded rear perspective view of a goggle and a pair of clips attached to a clip liner.
Figure 23:
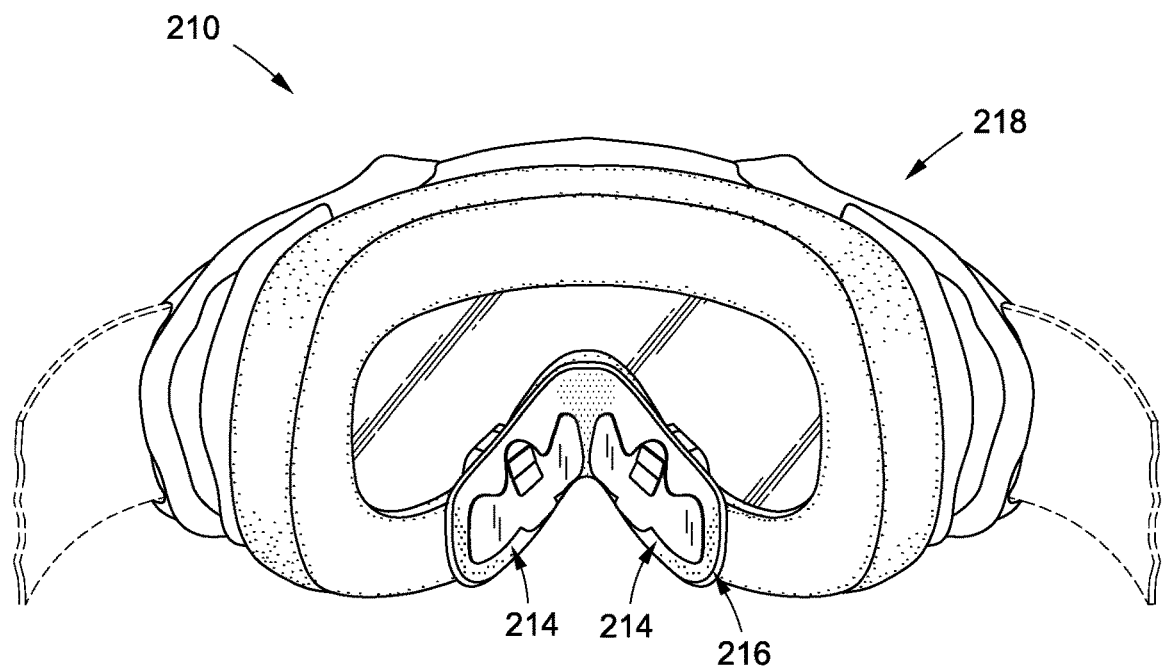
FIG. 23 is a rear perspective view of the pair of clips and the clip liner attached to the goggle.
Figure 24:
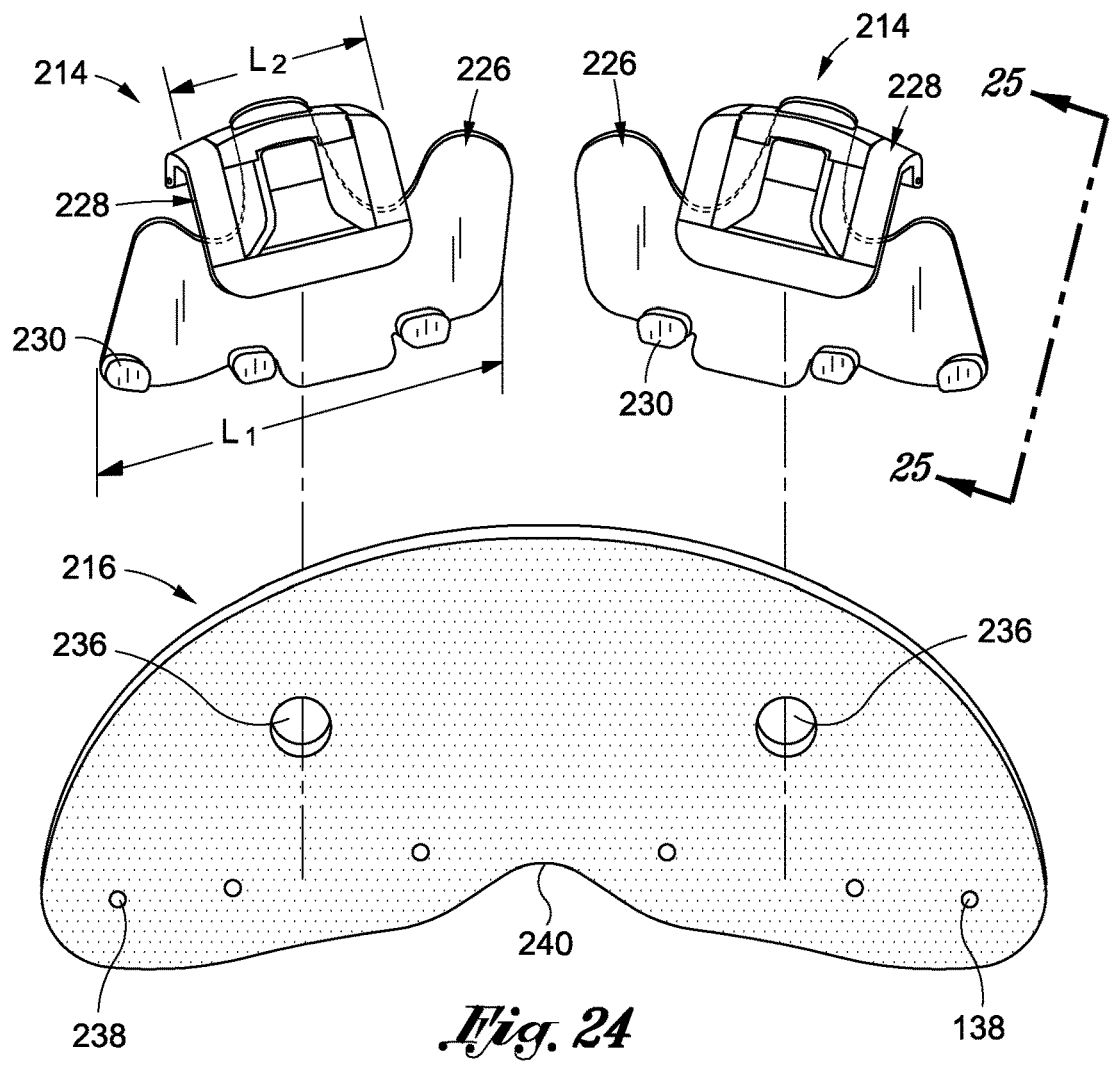
FIG. 24 is an exploded perspective view of the clips and clip liner of the breathing enhancement system depicted in FIG. 20.
Figure 25:
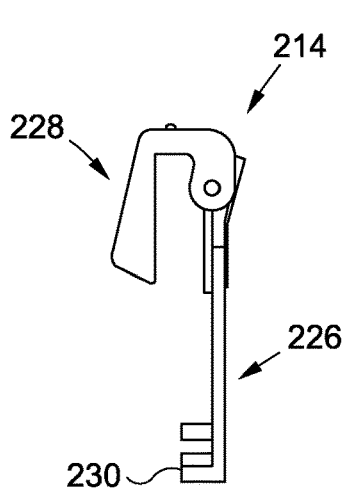
FIG. 25 is a side view of a clip depicted in FIG. 24.
Figure 26:
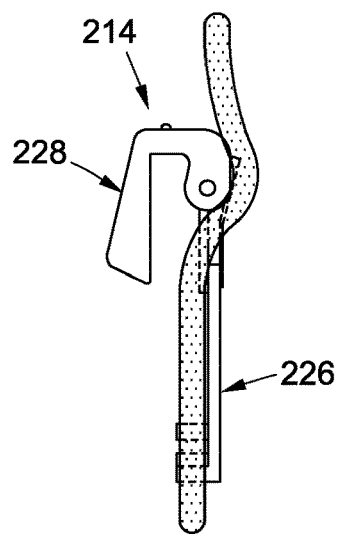
FIG. 26 is a side view of the clip depicted in FIG. 25 attached to the clip liner depicted in FIG. 24.
Figure 27:
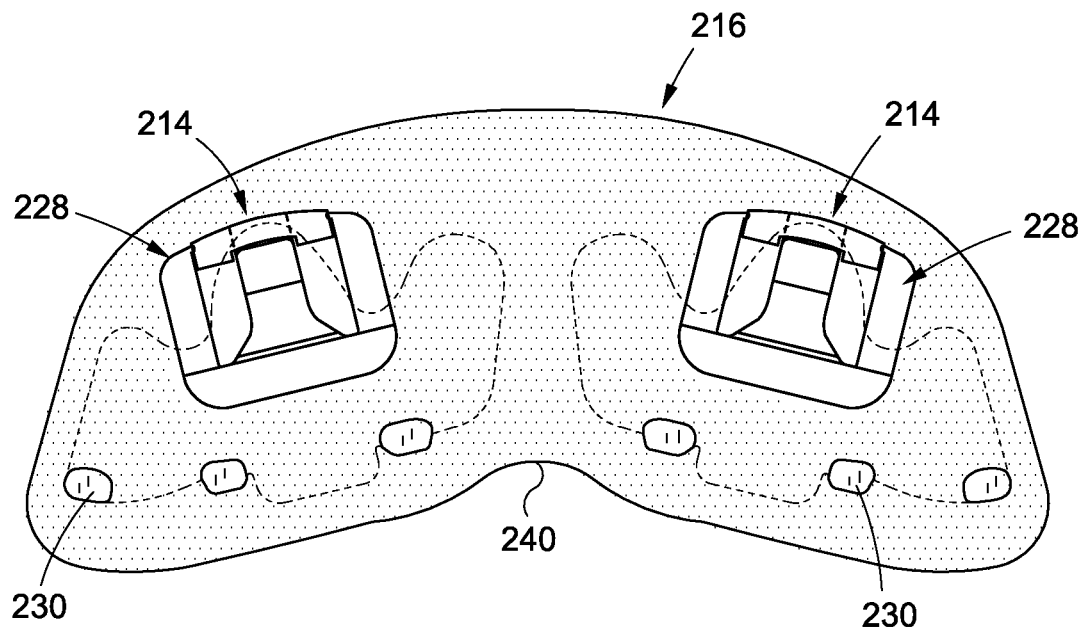
FIG. 27 is a rear view of the clips attached to the clip liner.
Figure 28:
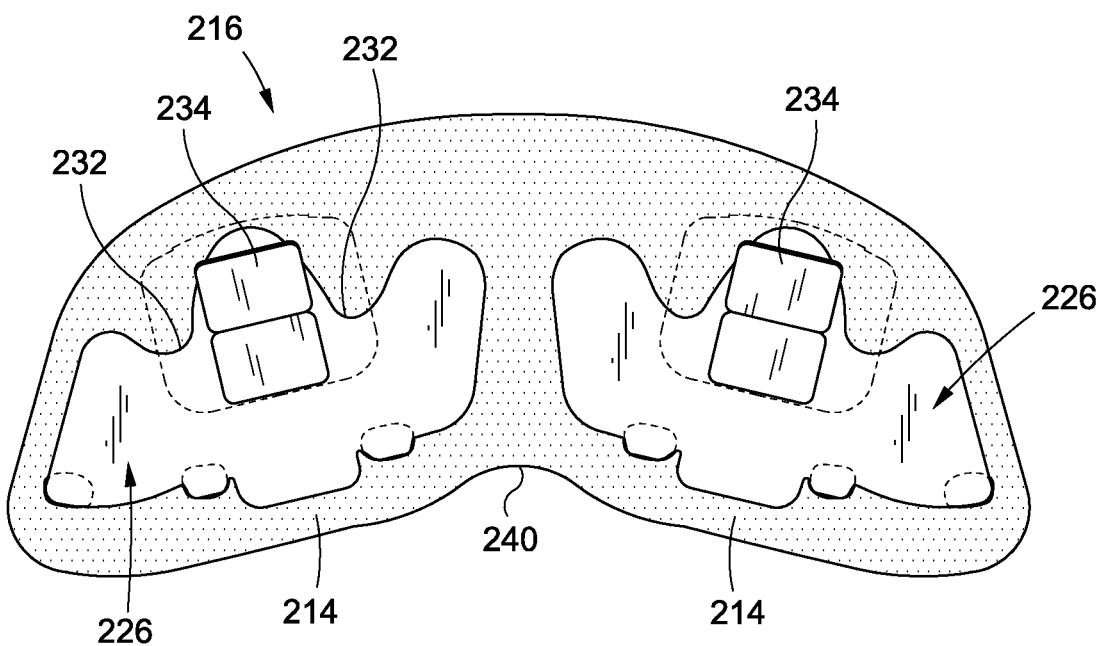
FIG. 28 is a front view of the clips attached to the clip liner.

Referring now to FIGS. 17-19, there is depicted various alternatives to the embodiment described above in relation to FIGS. 1-16. In particular, FIGS. 17-19 show a nasal attachment member 115 including a single nasal strip having a pair of attachment regions 117 on opposed ends of the nasal strip. Each attachment region 117 includes a ferrous body configured to be selectively engageable with a magnet 70 on a corresponding clip 38. The nasal strip 115 preferably includes an adhesive layer to allow the nasal strip 115 to be coupled to the wearer's nose 18.

FIGS. 18 and 19 also show an additional embodiment of a set of goggles 116 having magnets 170 coupled thereto without the use of a separate clip. The goggles 116 include a frame 120 having a frame opening with a lens 122 positioned therein. The frame 120 includes opposed lateral end portions 124, 126, a top portion 128, and an opposing bottom portion 130 having a bridge section 132 which fits over the nose 18 of the wearer 14. A headband or strap 134 may be connected to the opposed lateral end portions 124, 126 of the frame 120 for securing the frame 120 to the wearer's head.

In the embodiment depicted in FIGS. 18 and 19, the magnets 170 are located within the frame 120 between the inner and outer surfaces 123, 125 of the frame 120 and on opposite sides of the bridge apex. The magnets 170 may be embedded within the frame 120, or alternatively, located within a slot formed within the frame 120 to enable removal and replacement of the magnets 170. When the goggles 116 are worn by the wearer 14, the magnets 170 are positioned such that the magnets 170 are magnetically attracted to the magnets in the nasal attachment member 115.

The goggles 116 may be used with various implementations of the nasal attachment member, including a single nasal strip or separate nasal elements. In this respect, although the goggles 116 are specifically shown in FIGS. 18 and 19 as being used with a pair of nasal attachment members 117, it is also contemplated that the goggles 116 may also be used with the nasal strip 15 depicted in FIG. 1.

Those skilled in the art will readily appreciate that although the foregoing discussion describes the magnets as being incorporated in the clip or goggles, and the ferrous body being incorporated into the nasal element or nasal strip, other embodiments may have a reverse configuration, i.e., the magnet is incorporated into the nasal element or nasal strip and the ferrous body is incorporated into the clip or goggle.

It is contemplated that the system 10 may be packaged and sold as a complete set, including goggles, clips and nasal attachment member(s). Alternatively, the clips and nasal attachment member(s) may be sold separately as a set or individually. For instance, the system 10 may be sold as a kit, including two clips, four foam liners for the clips, wherein the foam liners are of two different foam thicknesses, as well as eight nose elements. Of course, other kits may include different numbers of items without departing from the spirit and scope of the present invention.

Referring now to FIGS. 20-28, there is depicted another embodiment of a breathing enhancement system 210 which generally includes a pair of nasal appliques 212, a pair of clips 214, and a clip liner 216. The breathing enhancement system 210 shown in FIGS. 20-28 is adapted for use with eyewear, such as goggles 218.

Each nasal applique 212 generally includes a base layer, a cover layer and a metallic element 220 located between the base layer and the cover layer, similar to the cross sectional configuration depicted in FIG. 15. The nasal applique 212 includes a peripheral configuration similar to an hour-glass or butterfly, and in this respect, includes two enlarged end portions 222 and a narrow middle portion 224. The narrow middle portion 224 is defined by a pair of opposed cutouts. When the nasal applique 212 is applied to the nose, the cutouts are placed over the crease on the user's nose that extends generally around a flared nostril. This provides a cutout around the crease of the user's nose, which becomes very active when breathing. Having that portion of the nose uncovered allows for dilating and breathing motion without initiating peeling of the applique. The opposed cutouts allow for use of the applique 212 on either side of the user's nose. However, it is also contemplated that the applique 212 may be specifically formed for use on only one side of the nose, and thus, such appliques may only have one cutout.

According to one embodiment, the base layer and cover layer are both configured to extend radially outward beyond the outer periphery of the metallic element 220 to define a peripheral ring portion. As such, the metallic element 220 is positioned over a central region of the base layer and is surrounded by a peripheral region of the base layer. In the exemplary embodiment, the outer peripheries of the cover layer and the base layer are substantially equal. However, it is understood that prior to being joined to the metallic element 220 and base layer, the cover layer may define a peripheral dimension that is larger than the base layer so as to accommodate the thickness of the metallic element.

The metallic element 220 may take on many forms, including a solid metallic disc, or alternatively, the metallic element may include a metallic powder, which may be embedded within the applique 212 (e.g., located between the base layer and the cover layer) or spread over an outer surface of the applique. Essentially, the metallic element 220 may include any form or configuration that may be magnetically attractable to a respective one of the clips.

An adhesive may be applied to the outer surface of the base layer to facilitate attachment of the applique 212 to the user's nose. According to one embodiment, the adhesive is adapted to increase the adhesive force between the base layer and the user's skin after remaining on the user's skin for a period of time. For instance, one particular adhesive may be adapted to impart a larger adhering force between the user's skin and the base layer approximately four minutes after being applied to the user's skin. In this respect, the adhesive is considered to have a "residency period" as the time between the initial placement of the applique 212 on the user's skin and the time at which the magnitude of the adhesive force reaches a maximum magnitude. It is understood that the residency period may vary from one adhesive to the next, and may be as small as a couple seconds, and as long as several minutes. The benefit of having an adhesive adapted to become stronger over time is that as the user begins to use the applique, the increasing adhesive strength mitigates inadvertent removal of the applique from the user's skin. Thus, although the user may begin to sweat and participate in rigorous physical activity while wearing the applique 212, the bond between the user's skin and the applique 212 may actually become stronger after initial placement of the applique 212 on the user. The adhesive may include polyethylene tape, polyolefin tape, or other adhesives known in the art to increase their adhesive strength over time. Exemplary adhesives are manufactured by 3M and include 1503 tape, 1521 tape, 1523 tape, 1525L tape, 1526 tape, 9865 tape, 1527 tape, 1527L tape, 1527EP tape, 9835 tape. Of course, those skilled in the art will readily appreciate that other adhesives may also be used without departing from the spirit and scope of the present disclosure.

The nasal appliques 212 are adapted to interface with metallic elements located on respective ones of the pair of clips 214. Both clips 214 are coupled to the clip liner 216, which includes a bridge section extending between the clips 214. According to one embodiment, each clip 214 includes a first clip member 226 and a second clip member 228 pivotally connected to the first clip member 226 via a hinge. The first and second clip members 226, 228 form opposing locking members defining a clip channel therebetween sized and adapted to receive a portion of the goggle frame to allow the clip 214 to clamp onto the goggle frame. The first and second clip members 226, 228 may be configured to be selectively locked (closed) and unlocked (open), as described above in relation to the clips shown in FIGS. 1-19.

According to one embodiment, the first clip member 226 includes a primary wall having a pair of opposed lateral edges defining a maximum first length, $L_1$ (see FIG. 24), which is larger than a second length, $L_2$, defined by the distance between opposed lateral edges of the second clip member 228. The primary wall includes a plurality of tabs 230 adapted to extend through corresponding openings formed in the liner 216, as will be described in more detail below. In the exemplary embodiment, the tabs 230 are located adjacent a bottom edge of the primary wall, although the tabs 230 may be located at other locations of the primary wall.

The primary wall may further include a pair of cutouts 232 (see FIG. 28) along an edge opposite the tabs 230 and adjacent the second clip member 228, to facilitate advancement of the middle portion of the first clip member 226 through an opening formed in the liner 216. In this respect, once advanced through the liner 216, the liner 216 may reside within the cutouts 232 formed within the primary wall.

One or more magnets 234 is connected to the clip 214 at an engagement region of the clip 214. As shown in the figures, the magnets 234 reside within a cavity formed in the first clip member 226.

As noted above, the liner 216 is adapted to engage with both clips 214 at the same time. According to one embodiment, the liner 216 includes a sheet of compressible material, such as foam, with the sheet including a plurality of openings formed therein, the openings being sized and adapted to allow the clips 214 to be engaged to the liner 216. In particular, the liner 216 includes a pair of primary openings 236 each being sized to receive the second clip member 228 of one of the clips 214, and a plurality of secondary openings 238 each being sized to receive one of the tabs 230 formed on the clips 214. It is contemplated that the liner 216 is formed of a resilient material to allow the openings 236, 238 to expand around the clip member or tab and contract around the clip member or tab for securing the liner 236 to the clip 214.

The liner 216 further includes an outer periphery which includes an arcuate section 240 located in the middle of the liner 216, with the arcuate section 240 being adapted to facilitate flexing or bending of the liner 216 to accommodate the contour of the goggle 218 and the anatomy of the wearer. The liner 216 may bend or flex about an axis, with the liner 216 having a substantially symmetrical configuration about the axis. In this respect, the pair of primary openings 236 may be disposed on opposite sides of the axis, and an equal number of secondary openings 238 may be disposed on opposite sides of the axis.

In order to use the breathing enhancement system 210 shown in FIGS. 20-28, the user applies the nasal appliques 212 to both sides of the user's nose by placing a first nasal applique on a first lateral region (e.g., the ala of the nose) adjacent a first nostril opening, and a second nasal applique on a second lateral region adjacent a second nostril opening. Typically, the appliques 212 are placed on the nose near the transition of the nose bone. The adhesive located on the applique creates an adhesive force between the applique and the user's nose to secure the applique to the nose. The adhesive is preferably adapted to increase the adhesive force while the applique remains on the user's nose for a prescribed residency time.

The clips 214 are coupled to the liner 216 by passing each second clip member 228 through a respective one of the primary openings 236, and the clip tabs 230 through respective ones of the secondary openings 238. The clips 214 are then attached to the goggle frame, such that when the clips 214 are secured to the frame, the goggle liner is compressed in the region adjacent the clips 214, with such compression oftentimes extending into the bridge region of the goggle. The clip liner 216 resides within the compressed region to maintain a "seal" or barrier against the user's faces to prevent debris (e.g., snow, dirt, etc.) from entering the area between the goggles 218 and the user's eyes. In this respect, the clip liner 216 extends between both clips 214 so as to reside within the compressed area of the goggle liner which may form between the clips 214 when the clips 214 are attached to the goggle 218.

After the clips 214 are secured to the goggle 218, and the appliques 212 are placed on the user's nose, the goggle 218 may be placed over the wearer's face. As the goggle 218 is moved into position, the magnets 234 on the clips 214 are moved closer to the metallic elements 220 on the appliques 212, thereby creating a stronger magnetic attraction therebetween, which in turn "activates" the system. The magnetic attraction draws the metallic element 220 of the applique 212 toward the magnet 234 in the clip 214, which dilates the wearer's nose to enhance the user's breathing.

One particular advantage of the breathing systems described herein is the ability of such systems to selectively transition between an ON (engaged) state and an OFF (disengaged) state without removing the nasal appliques from the user's nose. In the ON state, the nasal appliques are applied to the user's nose, and the clip or goggles carrying the magnet is engaged with the nasal appliques, which results in the dilating force being imparted on the user's nose. The breathing system may transition from the ON state to the OFF state by removing goggles (carrying the magnets) from the nasal appliques, which stops the application of the dilating force on the user's nose. In this regard, when the system is in the OFF state, the system is inactive. If the user subsequently wants to turn the system back ON, the user simply re-applies the goggles over the nose and into engagement with the nasal appliques.

The ability to selectively transition the system between ON and OFF states may be particularly advantageous, particularly when participating in sports-related activities, where the user may take breaks from time-to-time. For instance, many sports relates activities are divided into heats, periods, quarters, halves, etc., such that the user experiences extended periods of inactivity between extended active periods. The user may want to transition the system to the OFF state during periods of inactivity, and to the ON state during periods of activity. The configuration of the nasal appliques and the associated goggles allows for such quick and easy transition to give the user the enhanced ability to breathe when needed during the active periods. The selective transition of the system between an ON state and an OFF state may be analogous to a quarterback taking his mouthpiece out between plays.

The particulars shown herein are by way of example only for purposes of illustrative discussion, and are not presented in the cause of providing what is believed to be most useful and readily understood description of the principles and conceptual aspects of the various embodiments of the present disclosure. In this regard, no attempt is made to show any more detail than is necessary for a fundamental understanding of the different features of the various embodiments, the description taken with the drawings making apparent to those skilled in the art how these may be implemented in practice.

What is claimed is:

1. A disposable apparatus attachable to a nose of a wearer and useable with an external magnetic element positioned adjacent to the nose of the wearer, the disposable apparatus comprising:
   a flexible base layer including a first surface and an opposing second surface;
   an adhesive disposed on the first surface of the flexible base layer and capable of producing an adhesive force between the flexible base layer and the wearer for attaching the flexible base layer to the nose of the wearer, the adhesive being capable of increasing the adhesive force after the flexible base layer has been attached to the nose of the wearer; and
   a metallic element coupled to the second surface of the base layer and being magnetically interactable with the magnetic element when the magnetic element is positioned adjacent the nose of the wearer and the flexible base layer is attached to the nose of the wearer, the metallic element including a metallic disc having an arcuate surface extending away from the second surface of the base layer, the magnetic interaction between the metallic element and the magnetic element imparting a dilating force on the nose of the wearer causing the nose of the wearer to dilate, the metallic element being sized to reside adjacent only one of the nostrils on the nose of the wearer when the disposable apparatus is attached to the nose of the wearer;

the disposable apparatus being sized and shaped to be translatable relative to the magnetic element while the metallic element is magnetically coupled to the magnetic element;

the disposable apparatus being capable of residing on the nose of the wearer in an OFF state wherein no dilating force is imparted on the wearer by the disposable apparatus.

2. The disposable apparatus recited in claim 1, wherein the adhesive is capable of increasing the adhesive force after the flexible base layer has been attached to the nose of the wearer for a prescribed residency period.

3. The disposable apparatus recited in claim 1, wherein the adhesive includes polyethylene tape.

4. The disposable apparatus recited in claim 1, wherein the metallic element includes a metallic powder.

5. The disposable apparatus recited in claim 1, wherein at least a portion of the flexible base layer extends radially outward beyond the metallic element to define a flexible peripheral portion.

6. The disposable apparatus recited in claim 1, wherein the metallic disc defines a circular periphery.

7. A method of attaching a nasal applique to a nose of a wearer, the method comprising the steps of:
positioning the nasal applique on a lateral surface adjacent a nostril opening of the nose of the wearer, the nasal applique comprising:
a flexible base layer including a first surface and an opposing second surface;
an adhesive disposed on the first surface of the flexible base layer and capable of producing an adhesive force between the flexible base layer and the wearer for attaching the flexible base layer to the nose of the wearer, the adhesive being capable of increasing the adhesive force after the flexible base layer has been attached to the nose of the wearer; and
a metallic element coupled to the second surface of the base layer and being magnetically interactable with a remote magnetic element when the remote magnetic element is positioned adjacent the nose of the wearer and the flexible base layer is attached to the nose of the wearer, the metallic element being sized and shaped to be translatable relative to the magnetic element while the metallic element is magnetically coupled to the magnetic element, the magnetic interaction between the local metallic element and the remote magnetic element imparting a dilating force on the nose of the wearer causing the nose of the wearer to dilate, the metallic element being sized to reside adjacent only one of the nostrils on the nose of the wearer when the nasal applique is positioned on the lateral surface;
pressing the nasal applique on the lateral surface of the nose of the wearer to attach the nasal applique to the wearer; and
allowing the nasal applique to reside on the nose of the wearer in an OFF state prior to magnetic interaction with the remote magnet, wherein the nasal applique does not impart a dilating force on the wearer when the nasal applique is in the OFF state.

8. The method recited in claim 7, further comprising the step of allowing the nasal applique to remain on the wearer for a prescribed residency period, the adhesive force increasing during the residency period.

9. The method recited in claim 8, wherein the residency period is approximately four minutes.

10. A breathing enhancement system for use with eyewear having a compressible liner, the breathing enhancement system comprising:
a pair of clips selectively attachable to the eyewear and capable of compressing the compressible liner when attached to the eyewear to define a compressed portion of the compressible liner;
a clip liner engageable with and extendable between the pair of clips, the clip liner being capable of residing within the compressed portion of the compressible liner; and
a pair of nasal appliques selectively placeable on respective lateral portions the nose of a user, each nasal applique capable of being magnetically urged toward a respective one of the pair of clips in response to placement of the eyewear adjacent the nose of the user to cause the nasal passage of the user to open.

11. The breathing enhancement system recited in claim 10, wherein each nasal applique includes a base layer and an adhesive for producing an adhesive force between the base layer and the wearer for attaching the base layer to the nose of the wearer, the adhesive increasing the adhesive force after the base layer has been attached to the nose of the wearer.

12. The breathing enhancement system recited in claim 11, wherein the adhesive increases the adhesive force after the flexible base layer has been attached to the nose of the wearer for a prescribed residency period.

13. The breathing enhancement system recited in claim 11, wherein the adhesive includes polyethylene tape.

14. The breathing enhancement system recited in claim 10, wherein the clip liner is interfaceable with the user to mitigate the passage of particulate between the eyewear and the user when the pair of clips is attached to the eyewear and the eyewear is placed adjacent the nose of the user.

15. The breathing enhancement system recited in claim 10, comprising a pair of magnetic elements coupled to respective ones of the pair of clips and a pair of metallic elements coupled to respective ones of the pair of nasal appliques, the pair of magnetic elements being magnetically attractable to the pair of metallic elements.

16. The breathing enhancement system recited in claim 15, wherein the pair of magnetic elements include magnets, and the pair of metallic elements include metallic powder.

17. The breathing enhancement system recited in claim 10, wherein the clip liner includes a plurality of openings sized and shaped to receive respective ones of the pair of clips.

18. The breathing enhancement system recited in claim 10, wherein each clip includes a first clip member and a second clip member pivotally coupled to the first clip member.

19. The breathing enhancement system recited in claim 18, wherein the first clip member is pivotable relative to the second clip member between an open position and a closed position, an angle between the first and second clip members decreasing as the first and second clip members pivot from the open position toward the closed position.

20. The breathing enhancement system recited in claim 19, wherein the first and second clip members are lockable when the first and second clip members are in the closed position.

* * * * *